(12) United States Patent
Roques et al.

(10) Patent No.: US 7,169,574 B2
(45) Date of Patent: Jan. 30, 2007

(54) FLUORESCENCE DETECTION OF PROTEASES OR PEPTIDASES

(75) Inventors: Bernard Pierre Roques, Paris (FR); Nathalie Luciani, Paris (FR); Marie-Claude Fournie-Zaluski, Paris (FR); Hugues de Rocquigny, Versailles (FR)

(73) Assignees: Institut National de la Sante et de la Recherche Medicale (INSERM), Paris (FR); Centre National de la Recherche Scientifique (C.N.R.S.), Paris (FR)

( * ) Notice: Subject to any disclaimer, the term of this patent is extended or adjusted under 35 U.S.C. 154(b) by 149 days.

(21) Appl. No.: 10/240,923

(22) PCT Filed: Apr. 6, 2001

(86) PCT No.: PCT/FR01/01058

§ 371 (c)(1),
(2), (4) Date: Jun. 24, 2003

(87) PCT Pub. No.: WO01/77369

PCT Pub. Date: Oct. 18, 2001

(65) Prior Publication Data

US 2004/0214256 A1    Oct. 28, 2004

(30) Foreign Application Priority Data

Apr. 7, 2000    (FR) .................................. 00 04507

(51) Int. Cl.
| | |
|---|---|
| C12Q 1/37 | (2006.01) |
| C07K 7/04 | (2006.01) |
| C07K 7/08 | (2006.01) |
| C07K 2/00 | (2006.01) |
| A61K 38/00 | (2006.01) |
| A61K 38/02 | (2006.01) |
| G01N 33/53 | (2006.01) |
| A01N 37/18 | (2006.01) |

(52) U.S. Cl. .......................... 435/23; 435/24; 435/968; 530/300; 530/326; 530/327; 530/328; 530/329; 514/2

(58) Field of Classification Search ................ 435/23, 435/24, 968; 530/300; 514/2
See application file for complete search history.

(56) References Cited

U.S. PATENT DOCUMENTS

| | | | | | |
|---|---|---|---|---|---|
| 4,966,848 | A | * | 10/1990 | Smith et al. ................. | 435/193 |
| 5,223,421 | A | * | 6/1993 | Smith et al. ................. | 435/193 |
| 5,506,115 | A | * | 4/1996 | Toth et al. .................... | 435/23 |
| 5,708,137 | A | * | 1/1998 | Toth et al. ................... | 530/326 |
| 5,837,218 | A | * | 11/1998 | Peers et al. ................. | 424/1.69 |

OTHER PUBLICATIONS

Luciani et al, "Biochem. J.", V. 356(3), pp. 813-819, (Jun. 15, 2001)(Abstract Only).*
Murakami et al, "J. Amer. Chem. Society", V. 120(30), pp. 7520-7529, (Aug. 5, 1998)(Abstract Only).*
J. Rudinger. In: Peptide Hormones, JA Parsons, Ed. (1976) 1-7.*
D. Voet and J.G. Voet. Biochemistry, 2nd Edition.(1995), pp. 235-241.*
D.E. Smilek, et al. Proc. Natl. Acad. Sci. USA (1991) 88, pp. 9633-9637.*
W.S. Messer, "Vasopressin and Oxytocin", web document updated Apr. 3, 2000; http://www.neurosci.pharm.utoledo.edu/MBC3320/vasopressin.htm; 5 pages.*
T.J. Opgenorth, et al. FASEB Journal. (1992) 6, pp. 2653-2659.*
C. Anne, et al. Anal. Biochem. (2001) 291, pp. 253-261; published online Mar. 9, 2001.*
H. Mihara, et al. FEBS (1985) 193(1), pp. 35-38.*
A.G. Peranteau, et al. Anal. Biochem. (1995) 227, pp. 242-245.*
M. Mock and B.P. Roques. PNAS (2002) 99(10), pp. 6527-6529.*
T. Hohsaka, et al. J. Am. Chem. Soc. (1999) 121, pp. 12194-12195.*
M. Sisido and H. Kusano. Peptide Sci. (1999) pp. 65-66.*
N. Luciani, et al. Biochem. J. (2001) 356, pp. 813-819.*
T. Hohsaka, et al. J. Am. Chem. Soc. (1999) 121, pp. 34-40.*

* cited by examiner

*Primary Examiner*—Cecilia J. Tsang
*Assistant Examiner*—Andrew D. Kosar
(74) *Attorney, Agent, or Firm*—Stites & Harbison PLLC; B. Aaron Schulman

(57) ABSTRACT

The invention concerns the use of a PyA-$(Z)_x$-pNF group in a substrate for detecting, identifying and/or analyzing by fluorometry peptidases or proteases capable of cleaving the or a bond between a PyA and pNF and/or compounds with inhibiting or activating activity with respect to enzymes capable of cleaving said bond.

37 Claims, 3 Drawing Sheets

SEQUENCE LISTING

<160> NUMBER OF SEQ ID NOS: 17

<210> SEQ ID NO 1
<211> LENGTH: 22
<212> TYPE: PRT
<213> ORGANISM: Artificial sequence
<220> FEATURE:
<223> OTHER INFORMATION: Artificial peptides made up of amino acids wherein said peptides are used for the purpose of identifying compounds capable of inhibiting proteases or peptidases.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (1)..(1)
<223> OTHER INFORMATION: Xaa = any amino acid.
<220> FEATURE:
<221> NAME/KEY: MISC_FEATURE
<222> LOCATION: (2)..(2)
<223> OTHER INFORMATION: Xaa = any amino acid.
<220> FEATURE:
<221> NAME/KEY: MISC_FEATURE
<222> LOCATION: (5)..(5)
<223> OTHER INFORMATION: Xaa=Pyrenylalanine
<220> FEATURE:
<221> NAME/KEY: MISC_FEATURE
<222> LOCATION: (6)..(6)
<223> OTHER INFORMATION: Xaa=L-para-nitrophenylalanine
<220> FEATURE:
<221> NAME/KEY: MISC_FEATURE
<222> LOCATION: (20)..(20)
<223> OTHER INFORMATION: Xaa = any amino acid.
<220> FEATURE:
<221> NAME/KEY: MISC_FEATURE
<222> LOCATION: (21)..(21)
<223> OTHER INFORMATION: Xaa = any amino acid.
<220> FEATURE:
<221> NAME/KEY: MISC_FEATURE
<222> LOCATION: (22)..(22)
<223> OTHER INFORMATION: Xaa = any amino acid.

<400> SEQUENCE: 1

Xaa Xaa Ile Ile Xaa Xaa Asn Thr Pro Glu His Val Val Pro Tyr Gly

-continued

```
                1               5                  10                  15

Leu Gly Ser Xaa Xaa Xaa
            20

<210> SEQ ID NO 2
<211> LENGTH: 17
<212> TYPE: PRT
<213> ORGANISM: Artificial sequence
<220> FEATURE:
<223> OTHER INFORMATION: Artificial peptides made up of amino acids
      wherein said peptides are used for the purpose of identifying
      compounds capable of inhibiting proteases or peptidases.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa=Pyrenylalanine
<220> FEATURE:
<221> NAME/KEY: MISC_FEATURE
<222> LOCATION: (4)..(4)
<223> OTHER INFORMATION: Xaa=L-para-nitrophenylalanine

<400> SEQUENCE: 2

Ile Ile Xaa Xaa Asn Thr Pro Glu His Val Val Pro Tyr Gly Leu Gly
1               5                   10                  15

Ser

<210> SEQ ID NO 3
<211> LENGTH: 11
<212> TYPE: PRT
<213> ORGANISM: Artificial sequence
<220> FEATURE:
<223> OTHER INFORMATION: Artificial peptides made up of amino acids
      wherein said peptides are used for the purpose of identifying
      compounds capable of inhibiting proteases or peptidases.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (11)..(11)
<223> OTHER INFORMATION: AMIDATION
<220> FEATURE:
<221> NAME/KEY: MISC_FEATURE
<222> LOCATION: (7)..(7)
<223> OTHER INFORMATION: Xaa = Pyrenylalanine
<220> FEATURE:
<221> NAME/KEY: MISC_FEATURE
<222> LOCATION: (8)..(8)
<223> OTHER INFORMATION: Xaa = L-para-nitrophenylalanine

<400> SEQUENCE: 3

Arg Pro Lys Pro Gln Gln Xaa Xaa Gly Leu Met
1               5                   10

<210> SEQ ID NO 4
<211> LENGTH: 3
<212> TYPE: PRT
<213> ORGANISM: Artificial sequence
<220> FEATURE:
<223> OTHER INFORMATION: Artificial peptides made up of amino acids
      wherein said peptides are used for the purpose of identifying
      compounds capable of inhibiting proteases or peptidases.
<220> FEATURE:
<221> NAME/KEY: MOD_RES
<222> LOCATION: (1)..(1)
<223> OTHER INFORMATION: ACETYLATION
<220> FEATURE:
```

```
<221> NAME/KEY: MISC_FEATURE
<222> LOCATION: (3)..(3)
<223> OTHER INFORMATION: Xaa = Pyrenylalanine

<400> SEQUENCE: 4

Ile Ile Xaa
1

<210> SEQ ID NO 5
<211> LENGTH: 6
<212> TYPE: PRT
<213> ORGANISM: Artificial sequence
<220> FEATURE:
<223> OTHER INFORMATION: Artificial peptides made up of amino acids
      wherein said peptides are used for the purpose of identifying
      compounds capable of inhibiting proteases or peptidases.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (6)..(6)
<223> OTHER INFORMATION: Xaa = Pyrenylalanine

<400> SEQUENCE: 5

Arg Pro Lys Gln Gln Xaa
1               5

<210> SEQ ID NO 6
<211> LENGTH: 9
<212> TYPE: PRT
<213> ORGANISM: Artificial sequence
<220> FEATURE:
<223> OTHER INFORMATION: Artificial peptides made up of amino acids
      wherein said peptides are used for the purpose of identifying
      compounds capable of inhibiting proteases or peptidases.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Xaa = Pyrenylalanine
<220> FEATURE:
<221> NAME/KEY: MISC_FEATURE
<222> LOCATION: (5)..(5)
<223> OTHER INFORMATION: Xaa = any amino acid.
<220> FEATURE:
<221> NAME/KEY: MISC_FEATURE
<222> LOCATION: (6)..(6)
<223> OTHER INFORMATION: Xaa = L-para-nitrophenylalanine
<220> FEATURE:
<221> NAME/KEY: MOD_RES
<222> LOCATION: (9)..(9)
<223> OTHER INFORMATION: AMIDATION

<400> SEQUENCE: 6

Ser Lys Gly Xaa Xaa Xaa Gly Gly Lys
1               5

<210> SEQ ID NO 7
<211> LENGTH: 5
<212> TYPE: PRT
<213> ORGANISM: Artificial sequence
<220> FEATURE:
<223> OTHER INFORMATION: Artificial peptides made up of amino acids
      wherein said peptides are used for the purpose of identifying
      compounds capable of inhibiting proteases or peptidases.
<220> FEATURE:
<221> NAME/KEY: MOD_RES
<222> LOCATION: (1)..(1)
```

```
<223> OTHER INFORMATION: ACETYLATION
<220> FEATURE:
<221> NAME/KEY: MISC_FEATURE
<222> LOCATION: (4)..(4)
<223> OTHER INFORMATION: Xaa = Pyrenylalanine
<220> FEATURE:
<221> NAME/KEY: MISC_FEATURE
<222> LOCATION: (5)..(5)
<223> OTHER INFORMATION: Xaa = any amino acid.

<400> SEQUENCE: 7

Ser Lys Gly Xaa Xaa
1               5

<210> SEQ ID NO 8
<211> LENGTH: 10
<212> TYPE: PRT
<213> ORGANISM: Artificial sequence
<220> FEATURE:
<223> OTHER INFORMATION: Artificial peptides made up of amino acids
      wherein said peptides are used for the purpose of identifying
      compounds capable of inhibiting proteases or peptidases.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (10)..(10)
<223> OTHER INFORMATION: AMIDATION
<220> FEATURE:
<221> NAME/KEY: MISC_FEATURE
<222> LOCATION: (3)..(3)
<223> OTHER INFORMATION: Xaa = Pyrenylalanine
<220> FEATURE:
<221> NAME/KEY: MISC_FEATURE
<222> LOCATION: (8)..(8)
<223> OTHER INFORMATION: Xaa = L-para-nitrophenylalanine

<400> SEQUENCE: 8

Ser Gly Xaa Lys Ala Phe Ala Xaa Gly Lys
1               5                   10

<210> SEQ ID NO 9
<211> LENGTH: 5
<212> TYPE: PRT
<213> ORGANISM: Artificial sequence
<220> FEATURE:
<223> OTHER INFORMATION: Artificial peptides made up of amino acids
      wherein said peptides are used for the purpose of identifying
      compounds capable of inhibiting proteases or peptidases.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (3)..(3)
<223> OTHER INFORMATION: Xaa = Pyrenylalanine

<400> SEQUENCE: 9

Ser Gly Xaa Lys Ala
1               5

<210> SEQ ID NO 10
<211> LENGTH: 10
<212> TYPE: PRT
<213> ORGANISM: Artificial sequence
<220> FEATURE:
<223> OTHER INFORMATION: Artificial peptides made up of amino acids
      wherein said peptides are used for the purpose of identifying
      compounds capable of inhibiting proteases or peptidases.
<220> FEATURE:
```

```
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (10)..(10)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = Pyrenylalanine
<220> FEATURE:
<221> NAME/KEY: MISC_FEATURE
<222> LOCATION: (7)..(7)
<223> OTHER INFORMATION: Xaa = L-para-nitrophenylalanine

<400> SEQUENCE: 10

Ser Lys Gly Xaa Lys Ile Xaa Gly Gly Lys
1               5                   10

<210> SEQ ID NO 11
<211> LENGTH: 5
<212> TYPE: PRT
<213> ORGANISM: Artificial sequence
<220> FEATURE:
<223> OTHER INFORMATION: Artificial peptides made up of amino acids
      wherein said peptides are used for the purpose of identifying
      compounds capable of inhibiting proteases or peptidases.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Xaa = Pyrenylalanine

<400> SEQUENCE: 11

Ser Lys Gly Xaa Lys
1               5

<210> SEQ ID NO 12
<211> LENGTH: 10
<212> TYPE: PRT
<213> ORGANISM: Artificial sequence
<220> FEATURE:
<223> OTHER INFORMATION: Artificial peptides made up of amino acids
      wherein said peptides are used for the purpose of identifying
      compounds capable of inhibiting proteases or peptidases.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (10)..(10)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = Pyrenylalanine
<220> FEATURE:
<221> NAME/KEY: MISC_FEATURE
<222> LOCATION: (7)..(7)
<223> OTHER INFORMATION: Xaa = L-para-nitrophenylalanine

<400> SEQUENCE: 12

Ser Lys Gly Xaa Leu Lys Xaa Gly Gly Lys
1               5                   10

<210> SEQ ID NO 13
<211> LENGTH: 5
<212> TYPE: PRT
```

```
<213> ORGANISM: Artificial sequence
<220> FEATURE:
<223> OTHER INFORMATION: Artificial peptides made up of amino acids
      wherein said peptides are used for the purpose of identifying
      compounds capable of inhibiting proteases or peptidases.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Xaa = Pyrenylalanine

<400> SEQUENCE: 13

Ser Lys Gly Xaa Leu
1               5

<210> SEQ ID NO 14
<211> LENGTH: 9
<212> TYPE: PRT
<213> ORGANISM: Artificial sequence
<220> FEATURE:
<223> OTHER INFORMATION: Artificial peptides made up of amino acids
      wherein said peptides are used for the purpose of identifying
      compounds capable of inhibiting proteases or peptidases.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (9)..(9)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = Pyrenylalanine
<220> FEATURE:
<221> NAME/KEY: MISC_FEATURE
<222> LOCATION: (6)..(6)
<223> OTHER INFORMATION: Xaa = L-para-nitrophenylalanine

<400> SEQUENCE: 14

Ser Lys Gly Xaa Leu Xaa Gly Gly Lys
1               5

<210> SEQ ID NO 15
<211> LENGTH: 10
<212> TYPE: PRT
<213> ORGANISM: Artificial sequence
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (10)..(10)
<223> OTHER INFORMATION: AMIDATION
<220> FEATURE:
<221> NAME/KEY: MISC_FEATURE
<222> LOCATION: (4)..(4)
<223> OTHER INFORMATION: Xaa = Pyrenylalanine
<220> FEATURE:
<221> NAME/KEY: MISC_FEATURE
<222> LOCATION: (7)..(7)
<223> OTHER INFORMATION: Xaa = L-para-nitrophenylalanine

<400> SEQUENCE: 15

Ser Lys Gly Xaa Lys Phe Xaa Gly Gly Lys
1               5                   10

<210> SEQ ID NO 16
```

```
<211> LENGTH: 8
<212> TYPE: PRT
<213> ORGANISM: Artificial sequence
<220> FEATURE:
<223> OTHER INFORMATION: Artificial peptides made up of amino acids
      wherein said peptides are used for the purpose of identifying
      compounds capable of inhibiting proteases or peptidases.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Xaa = Pyrenylalanine
<220> FEATURE:
<221> NAME/KEY: MISC_FEATURE
<222> LOCATION: (8)..(8)
<223> OTHER INFORMATION: Xaa = L-para-nitrophenylalanine-OH

<400> SEQUENCE: 16

Ser Lys Gly Xaa Ala Gly Phe Xaa
1               5

<210> SEQ ID NO 17
<211> LENGTH: 6
<212> TYPE: PRT
<213> ORGANISM: Artificial sequence
<220> FEATURE:
<223> OTHER INFORMATION: Artificial peptides made up of amino acids
      wherein said peptides are used for the purpose of identifying
      compounds capable of inhibiting proteases or peptidases.
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (4)..(4)
<223> OTHER INFORMATION: Xaa = Pyrenylalanine

<400> SEQUENCE: 17

Ser Lys Gly Xaa Ala Gly
1               5
```

FLUORESCENCE DETECTION OF PROTEASES OR PEPTIDASES

The present invention relates, in general, to the use of a PyA-(Z)$_x$-pNF residue in substrates for peptidases or proteases, for the purposes of identifying and/or characterizing compounds capable of inhibiting these peptidases or proteases. It is in particular directed towards the use of such a residue, and more particularly the PyA-pNF residue, in a sequence for assaying endothelin-converting enzyme and/or identifying inhibitors of this enzyme.

The regulation of arterial blood pressure is under the control of several peptides which have either vaso-constricting actions on vessels (this is in particular the case with angiotensin II, endothelins and urotensin) or vasodilatory actions (this is in particular the case with bradykinin or with atrial natriuretic peptide, which also plays a role in the elimination of water and of sodium chloride).

Among all these peptides, endothelin-1 (ET-1), which is a peptide having a cyclic moiety, provided by two disulfide bridges, and a short linear moiety (FIG. 1) is considered to be a very powerful vasoconstrictor via action on the smooth muscles of the vessel walls, in particular at the cardiac level (coronary arteries).

Figure 2:
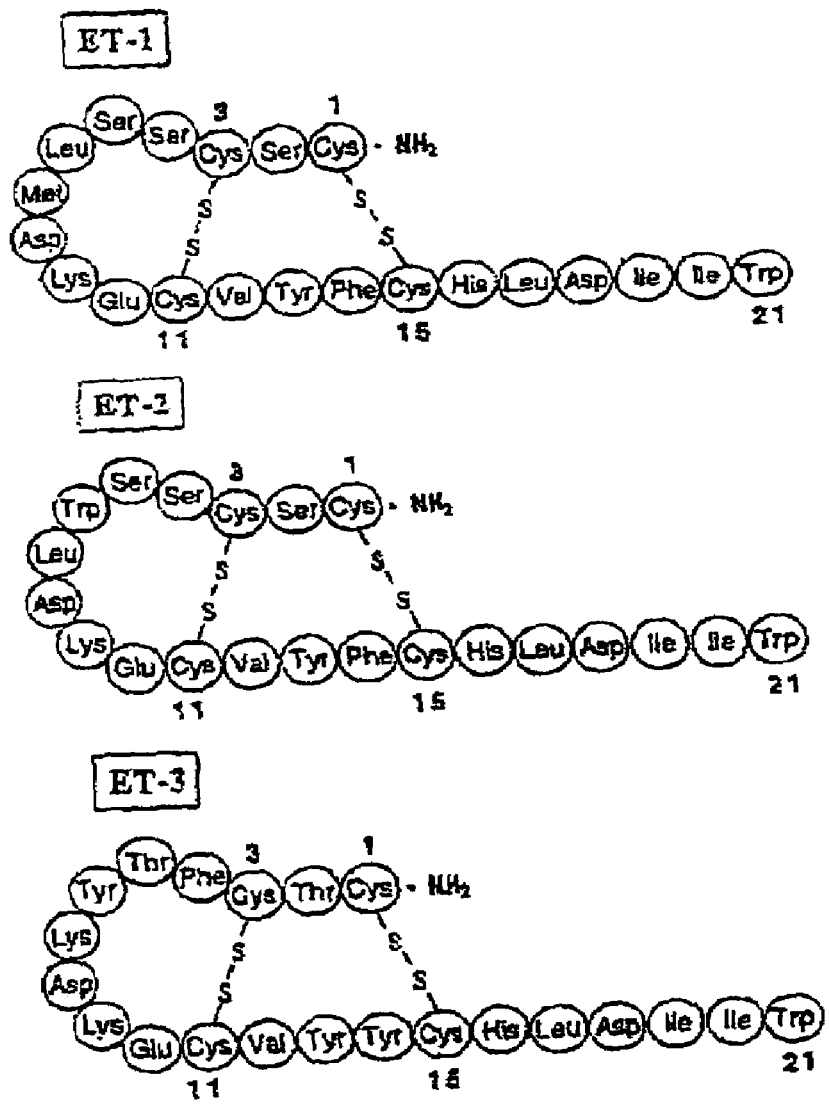

Endothelin-1 is part of a family of isopeptides which includes endothelin-2 (ET-2) and endothelin-3 (ET-3), which differ from ET-1 only by a few point changes of amino acids (FIG. 2).

Endothelins are secreted by endothelial cells in the form of inactive precursors, "big-endothelins", which are cleaved by zinc metallopeptidases named endothelin-converting enzyme (ECE), so as to give rise to the active peptides. Thus, taking the example of ET-1, ECE-1 hydrolyzes the Trp$^{21}$-Val$^{22}$ bond of big-endothelin-1, which comprises 38 amino acids, to generate two fragments, one of which, the N-terminal fragment, constitutes active endothelin-1. In the case of ET-3, it is the Trp$^{21}$-Ile$^{22}$ bond which is cleaved.

Big-ET-1 and ET-1 are detected in the plasma and ECE is a cytosolic or membrane-bound enzyme characterized, in this case, by a short intracellular fragment followed by a transmembrane helix of approximately 25 amino acids and a very large extracellular domain which contains the active site. The enzyme consists of two identical subunits linked by a disulfide bridge (Shimada et al., *Biochem. J.* (1996) 315, 863–867).

The administration of low doses of big-endothelin causes a large increase in arterial blood pressure, demonstrating cleavage of the precursor with formation of endothelin. This response can be blocked with an antagonist of the ET-1 receptor.

There is therefore a considerable advantage in inhibiting ECE with compounds for which there are potentially a very large number of applications in cardiovascular disorders. Mention may in particular be made of the treatment of myocardial infarction, of angina, of vascular spasms subsequent to a brain hemorrhage, of peripheral vessel spasms, of pulmonary hypertension, of cardiac and/or renal insufficiency, of disorders linked to diabetes and of asthma, and the prevention of restenoses and of cardiac and vascular fibroses.

In the case in point, certain cardiovascular pathologies might, consequently, be prevented or at least reduced by decreasing the circulating concentration of endothelins by inhibiting the enzyme which gives rise to them, that is to say ECE.

However, the intensive search for such inhibitors requires the availability of a simple identification test which can be automated, so as to allow a large number of assays to be carried out in a short period of time.

Now, the current tests are either difficult, long, relatively nonspecific and/or expensive.

The tests in which the two fragments produced by the action of ECE on big-ET are assayed by HPLC have the major drawback of requiring large amounts of enzyme and of big-ET.

The test based on the cleavage of iodine-125-labeled big-ET, producing $^{125}$I ET-1, and the determination thereof by attachment to its receptor, cannot be used for high throughput assays (Fawzi, A. B.; Clemen, R. M. & Wright, D. L. (1994) *Anal. Biochem.* 222, 342–350). The same is true of cell assays which measure the increase in cGMP induced by attachment of ET-1 to its receptor.

Radioimmunoassays, RIAS, require, for their part, a very complex series of successive experiments, are relatively poorly selective, and require the use of both big-ET and $^{125}$I ET-1. These complex assays are not suitable for the high throughput screening of very large series of potential inhibitors with automation of the test, and require the synthesis or purchase of radioactive iodinated endothelin, the time for use of which is limited.

More recently, a test has been proposed which is based on the use of a radioactive substrate obtained by the attachment of a tritiated propionyl residue to the N-terminal part of peptides of 21 amino acids containing the Trp-Val cleavage site (FR No. 96 02673). The radioactive N-terminal metabolite formed is extracted with an organic solvent, with stirring, and a sample of this solvent is removed and mixed with a scintillation fluid, and then the radioactivity is measured using a counter. Here again, the succession of steps does not make it possible to automate the assay and, in addition, requires the use of a radioelement and therefore the periodic synthesis of the tritiated substrate.

The object of the present invention is precisely to provide a novel assaying test which makes it possible to dispose of the drawbacks encountered with the tests mentioned above.

The present invention is based more particularly on the demonstration, by the inventors, that the use of pyrenylalanine (PyA) combined with the modified acid L-para-nitrophenylalanine (pNF) was particularly advantageous for diagnostic purposes.

Pyrenylalanine is a synthetic amino acid which has a considerable fluorescence capacity. Advantageously, this fluorescence of the PyA residue is virtually completely extinguished when PyA is placed close to, and preferably next to, the pNF residue.

Consequently, this natural fluorescence of PyA can only manifest itself from the moment this residue is no longer subjected to the repressor effect of the pNF residue, for example when it is physically separated from it, in particular by cleavage by a protease or peptidase, whatever the class (metallopeptidase, serine protease, aspartyl protease, cysteine protease) to which it belongs.

A residue of the PyA-pNF type therefore appears to be a particularly advantageous tool when it is introduced into a substrate, and more particularly into a peptide or pseudopeptide sequence, in order to visualize by fluorescence the manifestation of a cleavage.

A first aspect of the invention therefore relates to the use of a

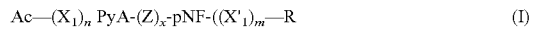

with Z representing a chain of amino acids of the L series, which may or may not be natural, and x representing 1 or 0, in a substrate for the purposes of detecting, identifying and/or assaying, by fluorescence, compounds liable to cleave the or a bond established between PyA and pNF and/or compounds with inhibitory or activating activity on known compounds capable of cleaving this bond.

The use claimed is most particularly advantageous for detecting, identifying and/or assaying, by fluorescence, compounds of the peptidase or protease type, whatever the group to which they belong, i.e. serine proteases, cysteine proteases, aspartyl proteases and metalloproteases.

The present invention is based on the appearance of a fluorescence caused by the separation of PyA and pNF by cleavage of a bond established between them.

Z may thus comprise up to 4 identical or different amino acids preferably selected from the list of the 20 natural amino acids. The length of the amino acid chain represented by Z is in fact to be adjusted depending on the substrate specificity of the peptidase and such that the distance separating PyA and pNF is compatible with the expression of the repressor effect of pNF on the fluorescence naturally emitted by PyA.

A second criterion for this adjustment is linked to the need to preserve the specificity and the affinity of the compound which naturally cleaves the substrate including $PyA-(Z)_x$-pNF. The choice of the $PyA-(Z)_x$-pNF residue is consequently made taking these two criteria into account.

The substrate into which the peptidyl residue $PyA-(Z)_x$-pNF is introduced is a peptide substrate.

A particular embodiment of the invention relates to the inclusion of a $PyA-(Z)_x$-pNF residue, and preferably PyA-pNF, in peptide sequences recognized by ECE. It is thus possible to identify, detect and/or assay ECE or ECE inhibitors or activators. Hydrolysis of the PyA-pNF residue produces a very strong increase in fluorescence (approximately from 150 to 800 times for a 5% degradation of the substrate).

According to a preferred embodiment of the invention, the dipeptidyl residue PyA-pNF is present, in the peptide sequence recognized by ECE, at the natural cleavage site for which it substitutes.

Unexpectedly, the dipeptidyl residue PyA-pNF proves to be cleavable by ECE and does not impair the affinity or the specificity of this enzyme for the peptide sequence which includes it.

In the particular case in which the peptide sequence corresponds to that of big-endothelin-1 or 2, the bond substituted is the $Trp^{21}$-$Val^{22}$ bond and when it corresponds to that of big-endothelin-3, the bond substituted is $Trp^{21}$-$Ile^{22}$.

The big-ET-1 (19–35) used as starting product can be prepared according to the usual methods, such as in particular using a solid-phase automatic synthesizer such as, for example, the 431A model of Applied Biosystems using Fmoc technology, as described in the reference E. Atherton and R. C. Sheppard (1989) *Solid Phase Peptide Synthesis: a practical approach*, IRL Press, Oxford.

The extreme sensitivity of the use claimed makes it possible to operate in very small volumes, of the order of 50 to 100 μl, with low concentrations of substrate of the order of 2 μM to 50 μM.

A second aspect of the invention relates to products of formula I:

in which
the symbols $X_1$ and $X'_1$ represent amino acids,
Z represents a chain of amino acids of the L series, which may or may not be natural, and x represents 1 or 0,
R represents an OH or $NH_2$ group,
Ac represents an acetyl group,
n is an integer ranging from 2 to 6 and m from 0 to 16, preferably from 3 to 13.

The test of the present invention is thus based on the use of peptides of formula (I), the N-terminal component of which is acylated, which has at least two advantages: to protect from cleavage by aminopeptidases and to reinforce the hydrophobicity of the N-terminal fragment which will be generated by hydrolysis.

This expression of fluorescence is linked to the generation in the cleavage of a metabolite of general formula II:

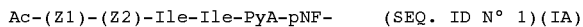

in which
$X_1$ and n are as defined above,
Z' represents one or more amino acids of the L series, which may or may not be natural, and
x represents 1 or 0.
More preferentially, x represents 0 in formulae (I) and (II).
According to a first variant of the invention, the compounds of formula (I) correspond to general formula (IA)

```
Ac-(Z1)-(Z2)-Ile-Ile-PyA-pNF-        (SEQ. ID N° 1)(IA)
AsN-Thr-Pro-Glu-His-Val-Val-Pro-
Tyr-Gly-Leu-Gly-Ser-(Z4)-(Z5)-
(Z6)-COOH
``` in which $Z_1$, $Z_2$, $Z_4$, $Z_5$ and $Z_6$, which may be identical or different, represent an amino acid.

More particularly, the compounds of formula I or IA are such that:
$Z_1$ and $Z_2$ are such that:
either $Z_1$ and $Z_2$ represent a single bond,
or $Z_1$ represents a single bond and $Z_2$ represents the amino acid Asp,
or $Z_1$ and $Z_2$ represent, respectively, the amino acids Leu and Asp,
$Z_4$, $Z_5$ and $Z_6$ are such that:
either $Z_4$, $Z_5$ and $Z_6$ represent a single bond,
or $Z_5$ and $Z_6$ represent a single bond and $Z_4$ represents the amino acid Pro,
or $Z_6$ represents a single bond and $Z_4$ and $Z_5$ represent, respectively, the amino acids Pro and Arg,
or $Z_4$, $Z_5$ and $Z_6$ represent, respectively, the amino acids Pro, Arg and Ser.

Substrates recognized by ECE are in particular covered by this general formula (IA).

As a representative indication of the substrates recognized by ECE and in accordance with general formula I, mention may most particularly be made of:

```
Ac-Ile-Ile-PyA-pNF-Asn-Thr-Pro-Glu-    (SEQ ID N° 2)
His-Val-Val-Pro-Tyr-Gly-Leu-Gly-Ser-
```

```
COOH

Ac-Arg-Pro-Lys-Pro-Gln-Gln-PyA-pNF-      (SEQ ID N° 3)

Gly-Leu-Met-NH₂ or

Ac-Ser-Gly-PyA-Lys-Ala-Phe-Ala-pNF-      (SEQ ID N° 8)

Gly-Lys NH₂.
```

SEQ ID No. 2 is, moreover, in accordance with general formula IA.

Similarly, as a representative indication of the metabolites of formula II, mention may in particular be made of:

```
   Ac-Ile-Ile-PyA                        (SEQ ID N° 4)

Ac-Arg-Pro-Lys-Gln-Gln-PyA or         (SEQ ID N° 5)

Ac-Ser-Gly-PyA-Lys-Ala                (SEQ ID N° 9)
```

According to a second variant of the invention, the compounds of general formula I correspond to general formula (IB)

```
Ac-Ser-Lys-Gly-PyA-(Z)ₓ-pNF-             (SEQ ID No. 6) (IB)

Gly-Gly-Lys-NH₂
``` with Z and x being as defined in general formula I.

According to this particular variant, the metabolite generated corresponds to general formula IIa

```
   Ac-Ser-Lys-Gly-PyA-(Z')ₓ              (SEQ ID No. 7)
``` with Z' and x as defined in general formula II.

By way of illustration of the substrates in accordance with formula IB of the invention, mention may in particular be made of:

as a substrate for kallikrein as a model of an enzyme of the serine protease family

```
Ac-Ser-Lys-Gly-PyA-Lys-Ile-pNF-          (SEQ ID n° 10)

Gly-Gly-Lys-NH₂

(metabolite formed:
Ac-Ser-Lys-Gly-PyA-Lys                   (SEQ ID No. 11))
``` as a substrate for papain as a model of an enzyme of the cysteine protease family

```
Ac-Ser-Lys-Gly-PyA-Leu-Lys-pNF-          (SEQ ID N° 12)

Gly-Gly-Lys-NH₂

(metabolite formed:
Ac-Ser-Lys-Gly-PyA-Leu                   (SEQ ID No. 13))
``` as a substrate for pepsin as a model of an enzyme of the aspartyl protease family

```
Ac-Ser-Lys-Gly-PyA-Leu-pNF-Gly-          (SEQ ID N° 14)

Gly-Lys-NH₂
```

```
(metabolite formed:
Ac-Ser-Lys-Gly-PyA-Leu                   (SEQ ID No. 13))
``` as a substrate for neprilysin as a model of an enzyme of the metalloendopeptidase family

```
Ac-Ser-Lys-Gly-PyA-Lys-Phe-pNF-          (SEQ ID N° 15)

Gly-Gly-Lys-NH₂

(metabolite formed:
Ac-Ser-Lys-Gly-PyA-Lys                   (SEQ ID No. 11))
``` as a substrate for ACE as a model of an enzyme of the metallodipeptidylcarboxypeptidase family

```
Ac-Ser-Lys-Gly-PyA-Ala-Gly-Phe-          (SEQ ID N° 16)

pNF-OH (metabolite formed:
Ac-Ser-Lys-Gly-PyA-Ala-Gly               (SEQ ID No. 17))
```

The preparation of the compounds in accordance with the present invention is within the competence of those skilled in the art.

The compounds claimed may be obtained by the usual methods of solid-phase synthesis according to the method of Merrifield on an automatic synthesizer such as, for example, the 431A device of Applied Biosystems. The chemistry used corresponds to Fmoc technology and protection of the side chains allowing cleavage thereof with trifluoroacetic acid as described by E. Atherton and R. C. Sheppard (1989) in "*Solid Phase Peptide Synthesis: a practical approach*, IRL Press, Oxford".

The acylation reaction so as to produce the compounds of formula I may be carried out under the usual conditions known to those skilled in the art.

The L-pyrenylalanine is obtained according to a method of asymmetric synthesis described in the publication J. M. Soleilhac et al., *Anal. Biochem.* (1996) 241, 120–127. The purity of the final peptides is estimated to be greater than 99% by reverse-phase HPLC and the identity of the peptides by electrospray mass spectrometry.

The couplings are carried out according to conventional techniques using a coupling agent such as HATU or PyBrop, and preferably using dicyclohexylcarbodiimide/hydroxybenzotriazole.

Another aspect of the present invention relates to the use of a compound of general formula I as defined above, for detecting, identifying and/or assaying a protease selected from the serine protease, cysteine protease, aspartyl protease and metallopeptidase family, and more preferentially ECE, and studying compounds capable of inhibiting or activating said enzyme.

According to a preferred variant of the invention, the compound to be assayed is either ECE or a compound capable of inhibiting or activating endothelin-converting enzyme.

A subject of the present invention is also a method for detecting, identifying and/or assaying a compound capable of inhibiting or activating endothelin-converting enzyme, characterized in that it comprises:

bringing a compound of general formula I, recognized by endothelin-converting enzyme, into contact, in solution, with said endothelin-converting enzyme and at least one compound liable to inhibit or activate ECE, measuring the fluorescence emitted in the presence, and where appropriate in the absence, of the compound to be detected, identified and/or assayed, and in that an absence of or a decrease in fluorescence indicates the presence of a compound which inhibits endothelin-converting enzyme.

In fact, the order in which the three compounds are brought into contact is not a determining factor. It is possible to bring the compound of general formula I into contact with ECE first of all, and then to introduce the presumed inhibitor or activator in a subsequent step.

According to another variant, the compound of general formula I is first brought into contact with the compound to be assayed and then the ECE.

The compound as defined above, to which the test defined above is applied in order to determine its ECE-inhibiting activity, may be diverse in nature, without limitation, and may, for example, be selected from phosphonimides, phosphamides and derivatives of these products, or else metalloproteinase inhibitors such as thiol derivatives, carboxylates or hydroxamates. As a compound, mention may also be made of phosphoramidon and N-(phenylethylphosphonyl)-Leu-Trp (TAKEDA), the ECE-inhibiting activities of which are known.

The compound to be tested may be in an isolated form, may be known or unknown and/or may be present in a compound library, a biological extract or water.

According to a preferred variant, the substrate is:

```
Ac-Ile-Ile-PyA-pNF-Asn-    (SEQ ID N° 2) (peptide 1s)

Thr-Pro-Glu-His-Val-Val-

Pro-Tyr-Gly-Leu-Gly-Ser-

COOH

Ac-Arg-Pro-Lys-Pro-Gln-    (SEQ ID N° 3) (peptide 2s)

Gln-PyA-pNF-Gly-Leu-Met-

NH₂. or

Ac-Ser-Gly-PyA-Lys-Ala-    (SEQ. ID N° 8) (peptide
                            3s)

Phe-Ala-pNF-Gly-Lys NH₂
```

The addition of increasing doses of a compound, capable of inhibiting the enzymatic activity of ECE on the substrate of general formula I for example, will result in a decrease in intensity of the fluorescence due to the metabolite, formed by the ECE, of formula Ac-Ile-Ile-PyA (peptide 1m), Ac-Arg-Pro-Lys-Gln-Glu-PyA (SEQ ID No. 5) (peptide 2m) or Ac-Ser-Gly-PyA-Lys-Ala (SEQ ID No. 9) (peptide 3m), the fluorescence of which is not modified over several hours. The measurement of this intensity, related to a standard curve established with mixtures of the substrate and of the fluorescent metabolite formed, therefore makes it possible either to evaluate the inhibitory capacity as percentage inhibition at a set given concentration of the product P, or to precisely determine its $IC_{50}$ and then its $K_I$ using the $K_m$ of the substrate and several concentrations of the product P. The extreme sensitivity of the assay makes it possible to operate in very small volumes (100 μl) with concentrations of the order of 20 μM of the substrate 1s (that is to say 2 nmole corresponding to 4.43 μg per assay) or 5 μM of the substrate 2s. The test can therefore be very easily used in 96 wells plates or more, making it possible to automate it with automatic determination of the $K_I$ values when the reading fluorimeter is connected to a computer having suitable commercial software.

When incubated with ECE, the peptides 1s, 2s and 3s produce only two metabolites, as shown by analysis of the reaction by HPLC, corresponding to the single cleavage at the PyA-pNF peptide bond.

Advantageously, these substrates are extremely selective since no cleavage is observed by HPLC after incubation for 2 h at 37° C. with purified zinc metallopeptidases belonging to the same family as ECE, such as, for example, neprilysin (NEP) or angiotensin-converting enzyme (ACE).

Finally, the sensitivity and the specificity of the test are such that it is possible to use both purified ECEs (Takahashi et al. *J. Biol. Chem.* (1993) 268, 21395–21398) and a membrane preparation of CHO cells into which ECE has been transfected (Xu et al. *Cell* (1994) 78, 473–485) or even a membrane preparation of an animal tissue rich in ECE (rat lung or brain). Since the sequence and the structure of ECE are very conserved from one species to another, which is particularly the case with rats and humans, the results ($K_I$ of inhibitors for example) obtained on purified or nonpurified rodent ECEs are identical to those obtained on the recombinant human enzyme.

The present invention therefore provides a test for identifying ECE inhibitors, and also determining the inhibitory capacities thereof, using a very rapid, reproducible fluorimetric assay allowing a very large number of tests which can be automated, and which can therefore be adapted to a high throughput selection of inhibitory molecules.

The present invention also provides the production of novel industrial products, which can optionally be used in the form of kits comprising ready-to-use 96-, 192- and 384-well plates containing either lyophilized ECE or a substrate as defined in general formula I and illustrated in the case of 1s, 2s and 3s, to which the reagents required to determine the inhibitory capacities of series of molecules are added, optionally using an automated device.

Another aspect of the invention relates to a method for diagnosing a pathology linked to an abnormal plasma level of endothelin-converting enzyme, characterized in that it uses a compound of the formula I as defined above.

The figures and examples below are presented by way of nonlimiting illustration of the present invention.

Figure 1:
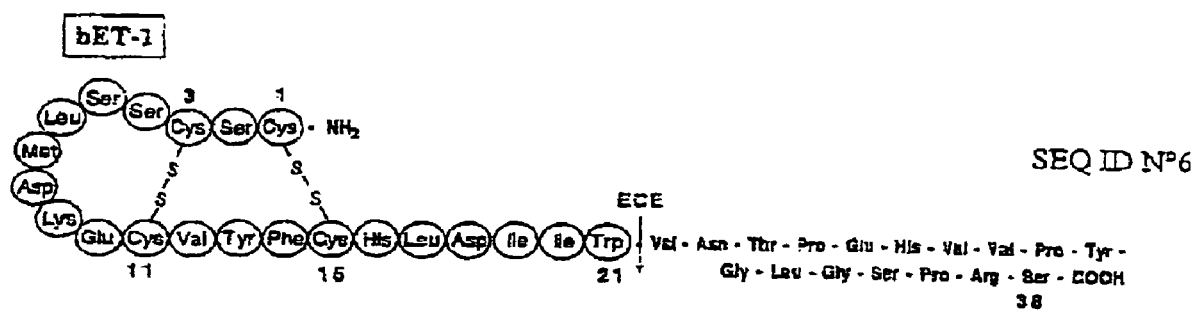

FIG. 1: peptide sequence of big-endothelin.

FIG. 2: peptide sequences of endothelins ET-1, ET-2 and ET-3.

Figure 3A:
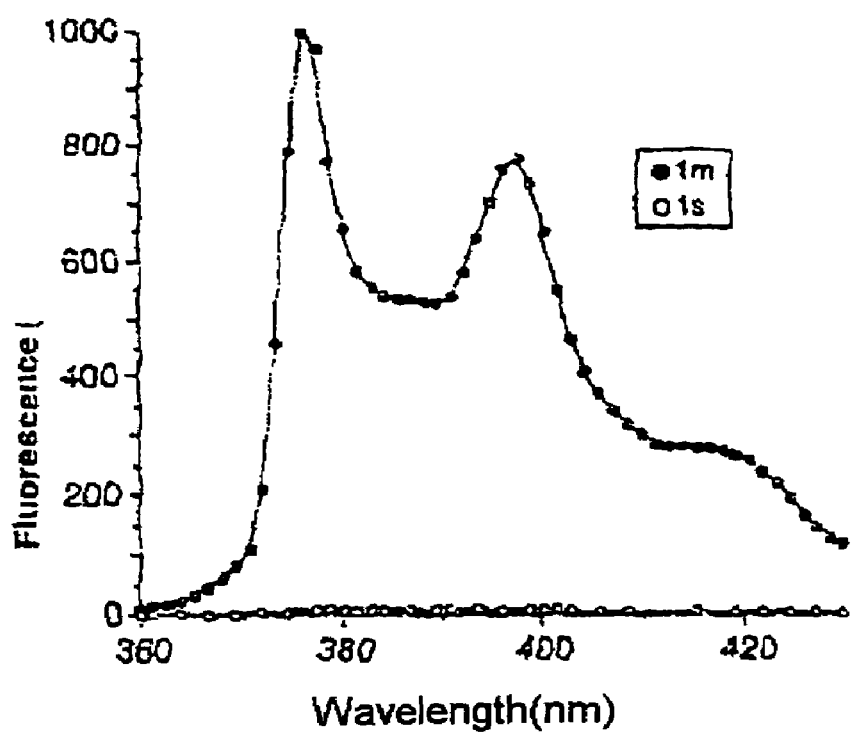
Figure 3B:
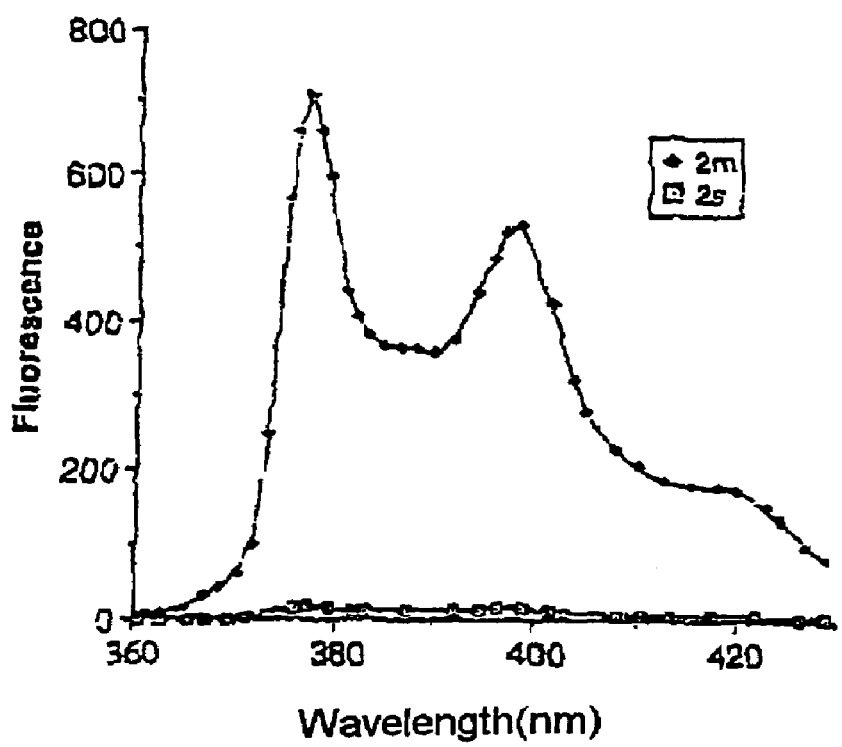

FIG. 3: graphs representing the fluorescence emission spectrum of the peptide 1s and of its metabolite 1m (FIG. 3*a*) and of the peptide 2s and of its metabolite 2m (FIG. 3*b*).

EXAMPLE 1

Preparation of Peptides

The peptides hereinafter identified as 1s and 2s and the corresponding fluorescent metabolites containing the pyrenylalanine residue are prepared in solid phase using the method of Merrifield on an automatic synthesizer using Fmoc strategy and protection of side chains generally in the form of a t-butyl, ether or ester, trityl or Boc residue as already described in "*Solid Phase Peptide Synthesis: A practical approach, IRL Press,* Oxford".

The couplings are carried out using dicyclohexyl-carbodiimide/hydroxybenzotriazole in N-methylpyrrolidone. The final peptide is obtained after cleavage and deprotection of the side chains with trifluoroacetic acid. The solution is evaporated under vacuum, and the peptide is precipitated with ether and purified by HPLC on a Vydac $C_{18}$ column.

The peptides are analyzed by mass spectrometry and $^1H$ NMR (400 or 600 MHz).

Compound 1s
Ac-Ile-Ile-PyA-pNF-Asn-Thr-Pro-Glu-  (SEQ ID No. 2)

His-Val-Val-Pro-Tyr-Gly-Leu-Gly-Ser-

COOH $MH^+_{(exp)}$: 2101.1; $MH^+_{(theo)}$: 2102.7

Compound 2s
Ac-Arg-Pro-Lys-Pro-Gln-Gln-PyA-pNF-  (SEQ ID No. 3)

Gly-Leu-Met-$NH_2$ $MH^+_{(exp)}$: 1558.8; $MH^+_{(theo)}$: 1559.7

These peptides can be conserved after lyophilization in the form of powder, in the dark and at 4° C. or at −20° C. for more than 6 months without deterioration. Similarly, the substrate stock solutions ($10^{-3}$–$10^{-4}$ M) can be conserved at 4° C. in the dark for several weeks.

EXAMPLE 2

2.1: Materials and Methods

Various preparations containing ECE can be used, such as, for example, recombinant human ECE-1c expressed in Cos-1 cells (Shimada et al., *J. Biol. Chem.* (1994) 269, 18275–18278) or CHO cells (Xu et al. *Cell* (1994) 78, 473–485).

In all cases, the presence of the enzyme is tested by Western blotting using an antibody and its concentration is evaluated by comparison with the purified enzyme.

The ECE activity is determined in 96-well plates, generally under the following conditions:

100 μl of 50 mM Tris-maleate buffer, pH 6.5, 20 μM or 5 μM of fluorescent peptide 1s or 2s and 10 μl of a solution of ECE diluted as a function of its purity and such that the cleavage of the fluorescent substrate remains less than 5%. Incubation is carried out for 20 minutes to 1 h, depending on the substrate used, from 20° C. to 37° C., in the presence or absence of a potential inhibitor at set concentrations (for example $5 \times 10^{-6}$ M and $10^{-6}$ M) or at increasing concentrations from $10^{-11}$ to $10^{-5}$ M so as to determine a $K_I$. The reaction is stopped in various ways, for example heating to 90° C., abrupt cooling to 4° C., adding an organic solvent such as dioxane to 20% of the final volume, and then the reading is performed using a fluorimeter ($\lambda_{ex}$=340 nm; $\lambda_{em}$=400 nm) optionally coupled to the automated analysis system. The use of a network fluorimeter considerably further increases the sensitivity of the assay by reading the fluorescence at 377 nm. The controls are performed in the presence of all the reagents but without ECE or with ECE inactivated beforehand by heating at 90° C. for 5 minutes. The $K_m$ values of the substrates (affinity constant of the enzyme for a substrate) calculated using the ENZFITTER program are:

1s, Km=22.1±0.9 μM;

2s,, Km=2±0.5 μM.

1s, Km=22.1±0.9 μM;
2s, Km=2±0.5 μM.

The $K_I$ values for the inhibitors can be determined automatically using the degradation percentages at various concentrations and comparison with a standard range. The fluorescence observed directly provides, after linearization, an $IC_{50}$ value, itself converted into $K_I$ using the Cheng-Prussof equation, $K_I=IC_{50}/1+([S]/K_m)$, with [S] being the concentration of substrate.

2.2: Assaying of ECE Activity with Respect to the Fluorescent Peptides 1s and 2s in the Absence of Inhibitors The fluorescence of the substrates 1s and 2s, and also that of their metabolites, was assessed in the absence of inhibitors. The protocol selected is that described previously.

FIGS. 3a and 3b report, respectively, the fluorescence emission spectra of the peptide 1s and of its metabolite 1m, and of the peptide 2s and of its metabolite 2m.

With regard to the products formed, the analysis thereof was carried out, in order to verify the substrate selectivity, by HPLC on a nucleosil $C_{18}$ column, 7 μm/300 Å (4.6×70 mm), using a buffer B (0.038% of TFA in $CH_3CN/H_2O$, 9/1 by vol.) and a gradient of 40–47% of buffer B in 10 minutes (flow rate 1 ml/min).

In all cases, a single cleavage site at the L.PyA-Lp.NF dipeptide was observed, generating only two metabolites.

EXAMPLE 3

The inhibitory behavior of several compounds was assessed by reproducing the protocol described in Example 2.

The compounds tested are:

| Negative controls | R = retrothiorphan |
| | T = thiorphan |
| | C = captopril |
| | L = lysinopril |
| Positive control | P = phosphoramidon |

The specific conditions selected for the assays appear below:

| | Blank* | Control | Test |
|---|---|---|---|
| Tris maleate, pH 6.5 | 90 μl | 80 μl | 70 μl |
| Inhibitor | / | / | 10 μl |
| Enzyme | / | 10 μl | 10 μl |

*The use of enzyme denatured with 6 N HCl or by heating at 80° C. for 10 minutes does not modify the residual fluorescence of the blank.

Preincubation is carried out for 10 minutes at 37° C. The ECE substrate is then added at an amount of 10 μM. The entire mixture is incubated for between 20 minutes and 1 hour at 37C and the reaction is then stopped either by cooling or by adding dioxane (20 μl).

The reading on cytofluor is performed at 4° C. with the following specificities: excitation 340 nm, emission 400 nm and with a gain of 85.

The assays are performed on a 96-well microplate.

Table I reports, for each well, the nature of the compound tested and also its concentration. The compounds were tested at two concentrations.

TABLE I

| 1 | 2 | 3 | 4 | 5 | 6 | 7 | 8 | 9 | 10 | 11 | 12 |
|---|---|---|---|---|---|---|---|---|---|---|---|
| Blank | | Control | | R $10^{-6}$ M | | R $5 \times 10^{-6}$ M | | T $10^{-6}$ M | | T $5 \times 10^{-6}$ M | |
| C $10^{-6}$ M | | C $5 \times 10^{-6}$ M | | L $10^{-6}$ M | | L $5 \times 10^{-6}$ M | | P $5 \times 10^{-6}$ M | | P $10^{-6}$ M | |

EXAMPLE 4

Table II shows the fluorescence intensity measured for each well. A low fluorescence value reflects strong inhibitory activity of the compound tested. The inhibitory behavior of the compound P is entirely verified.

TABLE II

| 1 | 2 | 3 | 4 | 5 | 6 | 7 | 8 | 9 | 10 | 11 | 12 |
|---|---|---|---|---|---|---|---|---|---|---|---|
| 67 | 68 | 1081 | 1094 | 1124 | 1106 | 1043 | 1077 | 1124 | 1127 | 1109 | 1121 |
| 1086 | 1089 | 1128 | 1121 | 1117 | 1093 | 1095 | 1119 | 140 | 133 | 455 | 459 |

---

The invention claimed is:

1. A method for detecting, identifying and/or assaying, by fluorescence, compounds likely to inhibit or activate a protease or peptidase which is capable of cleaving a peptide substrate comprising an amino acid sequence PyA-Z-pNF between PyA and pNF, with Z representing a chain of 0 to 4 natural amino acid(s) of the L series, which may be identical or different, said method comprising:

(1) contacting said substrate with said protease or peptidase, and optionally with at least one test compound likely to inhibit or activate the activity of said protease or peptidase; and (2) measuring the fluorescence emitted in the presence and in the absence of the test compound;

wherein an absence of, or a decrease in, fluorescence measured in the presence of the test compound, as compared with the fluorescence measured in the absence of the test compound, indicates the presence of a test compound with inhibitory activity on said protease or peptidase, or wherein an increase in fluorescence measured in the presence of the test compound, as compared with the fluorescence measured in the absence of the test compound, indicates the presence of a test compound with activating activity on said protease or peptidase.

2. The method according to claim 1, wherein said protease is selected from the serine protease, cysteine protease, aspartyl protease and metalloprotease families, and wherein said substrate is a compound of formula (I):

Ac—(X1)n PyA-Z-pNF-(X'1)m—R     (I)

in which:
X1 and X'1 represent, independently of one another, an amino acid,
Z represents a chain of 0 to 4 natural amino acid(s) of L series, which may be identical or different,
R represents OH or NH2,
Ac represents an acetyl group, and
n is an integer ranging from 2 to 6 and m from 0 to 16.

3. The method according to claim 1 wherein said protease is selected from the serine protease, cysteine protease, aspartyl protease and metalloprotease families, and wherein said substrate is a compound of formula (IB):

Ac-Ser-Lys-Gly-PyA-Z-pNF-Gly-Gly-Lys-NH2(IB) (SEQ ID NO: 6)

in which Ac represents an acetyl group, and Z represents a chain of 0 to 4 amino acid(s) of the L series, which may be identical or different.

4. The method according to claim 1 wherein said protease is endothelin converting enzyme (ECE) and said substrate is selected from the group consisting of a substrate having SEQ ID NO:2, SEQ ID NO:3 or SEQ ID NO:8.

5. The method according to claim 1, wherein said protease is endothelin converting enzyme (ECE) and said substrate comprises the amino acid sequence PyA-Z-pNF wherein Z represents a chain of 0 amino acid.

6. The method according to claim 1, wherein said protease is endothelin converting enzyme (ECE) and wherein a dipeptide which constitutes a cleavage site in a natural substrate cleaved by ECE is substituted by dipeptide PyA-pNF.

7. The method according to claim 6, wherein the natural substrate cleaved by ECE is big-endothelin-1 or big-endothelin-2 and the dipeptide substituted by PyA-pNF is Trp21-Val22.

8. The method according to claim 6, wherein the natural substrate cleaved by ECE is big-endothelin-3 and the dipeptide substituted by PyA-pNF is Trp21-Ile22.

9. The method according to claim 1, wherein the substrate has sequence SEQ ID NO: 10, and said protease is kallikrein.

10. The method according to claim 1, wherein the substrate has sequence SEQ ID NO: 12, and said protease is papain.

11. The method according to claim 1, wherein the substrate has sequence SEQ ID NO: 14, and said protease is pepsin.

12. The method according to claim 1, wherein the substrate has sequence SEQ ID NO: 15, and said protease is neprilysin.

13. The method according to claim 1, wherein the substrate has sequence SEQ ID NO: 16, and said protease is angiotensin converting enzyme.

14. A synthetic compound of formula (I):

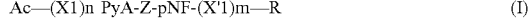

in which:
X1 and X'1 represent, independently of one another, an amino acid,
Z represents a chain of 0 to 4 natural amino acid(s) of L series, which may be identical or different,
R represents OH or NH2,
Ac represents an acetyl group, and
n is an integer ranging from 2 to 6 and m from 0 to 16.

15. The synthetic compound according to claim 14, that corresponds to formula (IB):

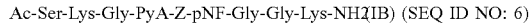

in which Z represents a chain of 0 to 4 natural amino acid(s) of the L series, which may be identical or different.

16. The synthetic compound according to claim 15, which is selected from the group consisting of:
Ac-Ser-Lys-Gly-PyA-Lys-Ile-pNF-Gly-Gly-Lys-NH2 (SEQ ID NO: 10),
Ac-Ser-Lys-Gly-PyA-Leu-Lys-pNF-Gly-Gly-Lys-NH2 (SEQ ID NO: 12,)
Ac-Ser-Lys-Gly-PyA-Leu-pNF-Gly-Gly-Lys-NH2 (SEQ ID NO: 14), and
Ac-Ser-Lys-Gly-PyA-Lys-Phe-pNF-Gly-Gly-Lys-NH2 (SEQ ID NO: 15).

17. The synthetic compound according to claim 14, wherein Z represents a chain of 0 amino acid.

18. The synthetic compound according to claim 17 of formula (IA):

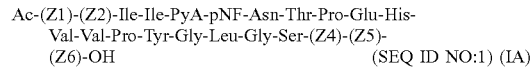

in which Z1, Z2, Z4, Z5 and Z6, which may be identical or different, represent independently of one another an amino acid or are a single bond.

19. The synthetic compound according to claim 18, wherein:
Z1 and Z2 are such that:
either Z1 and Z2 represent a single bond,
or Z1 represents a single bond and Z2 represents the amino acid Asp,
or Z1 and Z2 represent, respectively, the amino acids Leu and Asp,
Z4, Z5 and Z6 are such that:
either Z4, Z5 and Z6 represent a single bond,
or Z5 and Z6 represent a single bond and Z4 represents the amino acid Pro,
or Z6 represents a single bond and Z4 and Z5 represent, respectively, the amino acids Pro and Arg,
or Z4, Z5 and Z6 represent, respectively, the amino acids Pro, Arg and Ser.

20. The synthetic compound according to claim 14, which is selected from the group consisting of:
Ac-Ile-Ile-PyA-pNF-Asn-Thr-Pro-Glu-His-Val-Val-Pro-Tyr-Gly-Leu-Gly-Ser-OH (SEQ ID NO:2)
Ac-Arg-Pro-Lys-Pro-Gln-Gln-PyA-pNF-Gly-Leu-Met-NH2 (SEQ ID NO:3) and
Ac-Ser-Gly-PyA-Lys-Ala-Phe-Ala-pNF-Gly-Lys NH2 (SEQ ID NO:8).

21. The synthetic compound according to claim 14, which is Ac-Ser-Lys-Gly-PyA-Ala-Gly-Phe-pNF-OH (SEQ ID NO: 16).

22. A method for detecting, identifying and/or assaying a compound liable to inhibit endothelin-converting enzyme, that comprises:
contacting a compound of general formula (I), as defined in claim 14, recognized by endothelin-converting enzyme, in solution, with said endothelin-converting enzyme and at least one test compound liable to inhibit or activate ECE, and
measuring the fluorescence emitted in the presence and in the absence of the test compound to be detected, identified and/or assayed,
wherein an absence of, or decrease in, fluorescence measured in the presence of the test compound, as compared with the fluorescence measured in the absence of the test compound, indicates the presence of a compound which inhibits endothelin-converting enzyme.

23. The method according to claim 22, wherein the compound of general formula (I) is selected from the group consisting of:
Ac-Ile-Ile-PyA-pNF-Asn-Thr-Pro-Glu-His-Val-Val-Pro-Tyr-Gly-Leu-Gly-Ser-OH (SEQ ID NO:2)
Ac-Arg-Pro-Lys-Pro-Gln-Gln-PyA-pNF-Gly-Leu-Met-NH2 (SEQ ID NO:3) and
Ac-Ser-Gly-PyA-Lys-Ala-Phe-Ala-pNF-Gly-Lys NH2 (SEQ ID NO:8).

24. A method for detecting, identifying and/or assaying, by fluorescence, a protease or peptidase liable to cleave a peptide substrate comprising an amino acid sequence PyA-Z-pNF between PyA and pNF, with Z representing a chain of 0 to 4 natural amino acid(s) of the L series, which may be identical or different, said method comprising:

(1) contacting said substrate with a test compound; and
(2) measuring the level of fluorescence in the presence of the protease or peptidase,
wherein an increase of fluorescence measured in the presence of the protease or peptidase, as compared with fluorescence measured in absence of the protease or peptidase, is indicative of a protease or peptidase capable of cleaving said substrate between PyA and pNF.

25. The method according to claim 24, wherein said protease is selected from the serine protease, cysteine protease, aspartyl protease and metalloprotease families, and wherein said substrate is a compound of formula (I):

Ac—(X1)n PyA-Z-pNF-(X'1)m—R    (I)

in which:
X1 and X'1 represent, independently of one another, an amino acid,
Z represents a chain of 0 to 4 natural amino acid(s) of L series, which may be identical or different,
R represents OH or NH2,
Ac represents an acetyl group, and
n is an integer ranging from 2 to 6 and m from 0 to 16.

26. The method according to claim 24, wherein said protease is selected from the serine protease, cysteine protease, aspartyl protease and metalloprotease families, and wherein said substrate is a compound of formula (IB):

Ac-Ser-Lys-Gly-PyA-Z-pNF-Gly-Gly-Lys-NH2 (IB) (SEQ ID NO: 6)

in which Ac represents an acetyl group, and Z represents a chain of 0 to 4 amino acid(s) of the L series, which may be identical or different.

27. The method according to claim 26 wherein said substrate is selected from the group consisting of:
Ac-Ser-Lys-Gly-PyA-Lys-Ile-pNF-Gly-Gly-Lys-NH2 (SEQ ID NO: 10),
Ac-Ser-Lys-Gly-PyA-Leu-Lys-pNF-Gly-Gly-Lys-NH2 (SEQ ID NO: 12),
Ac-Ser-Lys-Gly-PyA-Leu-pNF-Gly-Gly-Lys-NH2 (SEQ ID NO: 14), and
Ac-Ser-Lys-Gly-PyA-Lys-Phe-pNF-Gly-Gly-Lys-NH2 (SEQ ID NO: 15).

28. The method according to claim 24 wherein said protease is endothelin converting enzyme (ECE) and said substrate is selected from the group consisting of a substrate having SEQ ID NO:2, SEQ ID NO:3 or SEQ ID NO:8.

29. The method according to claim 24, wherein said protease is endothelin converting enzyme (ECE) and said substrate comprises the amino acid sequence PyA-Z-pNF wherein Z represents a chain of 0 amino acid.

30. The method according to claim 24, wherein said protease is endothelin converting enzyme (ECE) and wherein a dipeptide which constitutes a cleavage site in a natural substrate cleaved by ECE is substituted by dipeptide PyA-pNF.

31. The method according to claim 30, wherein the natural substrate cleaved by ECE is big-endothelin-1 or big-endothelin-2 and the dipeptide substituted by PyA-pNF is Trp21-Val22.

32. The method according to claim 30, wherein the natural substrate cleaved by ECE is big-endothelin-3 and the dipeptide substituted by PyA-pNF is Trp21-Ile22.

33. The method according to claim 24, wherein the substrate has sequence SEQ ID NO: 10, and said protease is kallikrein.

34. The method according to claim 24, wherein the substrate has sequence SEQ ID NO: 12, and said protease is papain.

35. The method according to claim 24, wherein the substrate has sequence SEQ ID NO: 14, and said protease is pepsin.

36. The method according to claim 24, wherein the substrate has sequence SEQ ID NO: 15, and said protease is neprilysin.

37. The method according to claim 24, wherein the substrate has sequence SEQ ID NO: 16, and said protease is angiotensin converting enzyme.

* * * * *